United States Patent [19]

Roof et al.

[11] 4,007,626
[45] Feb. 15, 1977

[54] CHROMATOGRAPHIC ANALYSIS
[75] Inventors: Lewis B. Roof, Bartlesville, Okla.; Donald D. DeFord, Glenview, Ill.
[73] Assignee: Phillips Petroleum Company, Bartlesville, Okla.
[22] Filed: Apr. 18, 1975
[21] Appl. No.: 569,437
[52] U.S. Cl. .............................................. 73/23.1
[51] Int. Cl.² ........................................ G01N 31/08
[58] Field of Search ....... 73/23.1; 23/232 C, 254 R, 23/230 HC

[56] References Cited
UNITED STATES PATENTS

| | | | |
|---|---|---|---|
| 3,103,807 | 9/1963 | Broerman | 73/23.1 |
| 3,112,639 | 12/1963 | Maxwell | 73/23.1 |
| 3,372,573 | 3/1968 | Sanford et al. | 73/23.1 |
| 3,385,101 | 5/1968 | Roof | 73/23.1 |
| 3,394,582 | 7/1968 | Munro et al. | 73/23.1 |
| 3,715,910 | 2/1973 | Fore et al. | 73/23.1 |
| 3,720,092 | 3/1973 | Reinecke | 73/23.1 |

*Primary Examiner*—James J. Gill
*Assistant Examiner*—Stephen A. Kreitman

[57] ABSTRACT

Chromatographic analysis of the volatile components of a liquid having both volatile and nonvolatile components is accomplished by vaporizing the volatile portion of a liquid sample in a hollow tubular vaporizing column and subsequently analyzing the thus-vaporized portion of the sample. The nonvolatile components of the sample are retained in the vaporizing column during vaporizaton and then are removed by backflushing the vaporizing column with a preselected volume of a liquid solvent.

11 Claims, 5 Drawing Figures

CHROMATOGRAPHIC ANALYSIS

This invention relates to chromatographic analysis. In another aspect it relates to chromatographic anaylsis of liquid samples having nonvolatile components. In yet another aspect the invention relates to an apparatus and method for gas chromatographic analysis as a volatile portion of a liquid sample. In still another aspect the invention relates to an apparatus and method for automatically analyzing volatile components of a liquid sample. In another aspect the invention relates to an apparatus and method for analysis of successive samples having both volatile and nonvolatile consitutents.

It is often desirable to make a gas chromatographic analysis of the more volatile constituents in a liquid sample which contains constituents which are nonvolatile or are difficult to vaporize under ordinary gas chromatographic anaylsis conditions. One application in which the analysis of the more volatile constituents within a liquid sample is desirable would be the analysis of the lighter constituents of a crude oil sample containing, in addition to the lighter constituents, heavy asphaltic compounds or other similar heavy constituents. In such an application analysis of the heavier constituents can be accomplished separately or can be omitted when the primary purpose of the analysis is not to obtain the complete analysis of the sample but to analyze only the lighter, more volatile constituents of the sample.

While the use of liquid chromatography to analyze a liquid sample is effective in analyzing the entire liquid sample, the use of a gas chromatographic analysis of the volatilized portions of the liquid sample permits the use of more economical equipment and materials in obtaining an analysis of only the more volatile constituents. In general, previous methods and apparatus for performing such a gas chromatographic analysis have injected the liquid sample directly into a packed chromatographic column. The difficulty of backflushing the remaining liquid portion of the sample from the column following separation of the sample within the packed chromatographic column, however, can become a problem if the nonvolatile heavy constituents are not easily washed from the column packing material. In addition, backflushing the required type and amount of liquid solvent through the packed column to remove nonvolatile constituents therefrom can be destructive of the desirable properties of the chromatographic column packing material, particularly when the packing material comprises a liquid material phase on a solid base material. It is also important to accomplish backflushing of the remaining nonvolatile liquid of the sample in a manner which precludes interference with the analysis of subsequent samples which might otherwise be caused by traces of solvent remaining in the chromatographic apparatus.

Accordingly an object of the invention is to provide an improved method and apparatus for chromatographic analysis. Another object of the invention is to provide an apparatus and method for gas chromatographic analysis of a volatile portion of a liquid sample. An additional object of the invention is to provide an apparatus and method for automatically analyzing volatile components of a liquid sample. A further object of the invention is to provide an apparatus and method for analysis of successive samples having both volatile and nonvolatile constituents. Yet another object of the invention is to provide an apparatus and method for preventing backflush solvent interference with the analysis of subsequent samples. Another object of the invention is to provide a method and apparatus for separating preselected constituents within liquid samples having components of differing volatility.

In accordance with the invention a preselected volume of a liquid sample is introduced into a hollow, unpacked tubular column maintained at a temperature and pressure adequate to provide for volatilization of the sample constituents which are to be analyzed. The vaporized portion of the sample is then carried through a first packed chromatographic column wherein preliminary separation of the individual constituents of the volatilized portion of the sample is accomplished. Those vaporized portions of the liquid sample which are to be measured are then carried into a second packed chromatographic column. As soon as the constituents which are to be measured have entered the second packed chromatographic column, carrier gas backflushing of the first packed chromatographic column is utilized to remove the gaseous constituents having a relatively long elution time or any other remaining constituents from the first packed chromatographic column. The unpacked column is backflushed with a preselected volume of a suitable solvent liquid followed by the carrier gas from the first packed chromatographic column.

Additional objects and advantages of the invention will be apparent from the specification and claims and from a description of the preferred embodiment of the invention illustrated by FIGS. 1–5 wherein:

Figure 1:
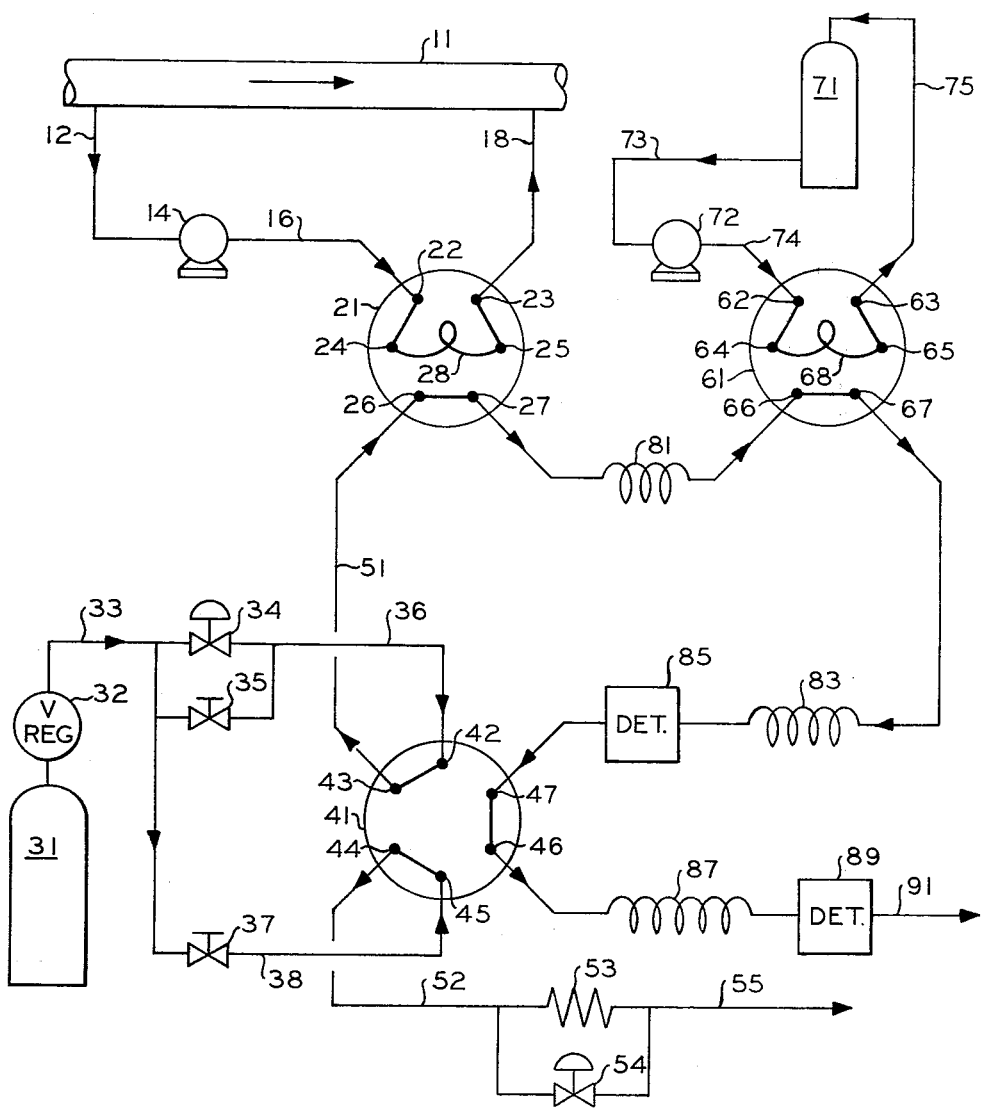
FIG. 1 is a schematic representation of the chromatographic apparatus of the invention showing the initial condition of the chromatographic system.

Referring now to FIG. 1, there is illustrated a liquid sample source 11 containing liquid material which is to be sampled and analyzed in accordance with the invention. The sample source 11 can be any suitable vessel, conduit, or other similar supply or source of the liquid material to be analyzed. Liquid material is removed from the sample source 11 through a conduit means 12. A pump means 14 maintains the desired flow of sample material to a sample valve 21 by delivering the sample material through a conduit 16 to the sample inlet port 22 of the sample valve 21. In addition to its sample inlet port 22, the sample valve 21 has a sample outlet port 23, a sample loop inlet port 24, a sample loop outlet port 25, a carrier inlet port 26, and a carrier outlet port 27. A sample loop 28 having a desired preselected volume is connected in operable fluid communication between the sample loop inlet port 24 and sample loop outlet port 25 of the sample valve 21. The characteristics of the sample valve 21 are such that in a first position illustrated by FIG. 1 the sample material delivered to the sample loop inlet port 22 via the conduit means 16 is delivered to the sample loop inlet port 24, flows through the sample loop 28 to the sample loop outlet port 25, is delivered to the sample outlet port 23 and is thereupon carried by a conduit means 18 back to the liquid sample source 11 or otherwise disposed of in a suitable manner. When there is an adequate pressure drop within the liquid sample source 11 between the points at which the conduit means 12 and 18 communicate therewith, a pump means 14 may not be required to maintain the desired flow of sample material through the sample loop 28 and the conduit means 12 may be connected directly to the sample inlet port 22 of the sample valve 21.

A carrier gas supply means 31 is connected through a regulating valve 32 to a carrier supply conduit means 33. An automatic valve means 34 and a flow control valve 35 are arranged in a parallel relationship to operably connect the carrier supply conduit means 33 with a first carrier stream conduit means 36. An additional flow control valve 37 operably connects the carrier supply conduit means 33 to a second carrier stream conduit means 38.

A backflush valve 41 has a first carrier stream inlet port 42, a sample valve port 43, a vent port 44, a second carrier stream inlet port 45, a downstream chromatographic column port 46, and an upstream chromatographic column port 47. The first carrier stream inlet port 42 of the valve 41 is operably connected to the first carrier stream conduit means 36. The sample valve port 43 is operably connected to the carrier inlet port 26 of the sample valve 21 by a conduit 51. The vent port 44 is connected by a vent conduit 52 to a suitable flow restriction means 53 and an automatic flow restriction bypass valve 54. The flow restriction means 53 and the bypass valve 54 operably connect the vent conduit 52 in fluid communication with a disposal conduit 55. In the first position of the backflush valve 41 illustrated by FIG. 1, the first carrier stream port 42 is in fluid communication with the sample valve carrier port 43, the vent port 44 is in fluid communication with the second carrier stream inlet port 45, and the downstream chromatographic column port 46 is in fluid communication with the upstream chromatographic column port 47.

The solvent valve 61 has a solvent inlet port 62, a solvent outlet port 63, a solvent loop inlet port 64, a solvent loop outlet port 65, a vaporizer column port 66, and a chromatographic column port 67. A solvent loop 68 having a desired preselected volume is connected between the solvent loop inlet port 64 and the solvent loop outlet port 65. A liquid solvent supply means 71 containing a supply of a liquid solvent suitable for dissolving the nonvolatilized constituents of a sample taken from the sample material supply means 11, is operably associated with a pump means 72 so that a flow of solvent from the solvent supply means 71 is withdrawn from source 71 through a conduit 73 and pumped via a conduit 74 to the solvent inlet port 62 of the solvent valve 61. The solvent leaving the valve 61 via the solvent outlet port 63 is returned to the solvent supply means 71 by a conduit 75. In the first position of the solvent valve 61 illustrated by FIG. 1, the solvent inlet port 62 is in fluid communication with the solvent loop inlet port 64, the solvent outlet port 63 is in fluid communication with the solvent loop outlet port 65, and the vaporizer column port 66 is in fluid communication with the chromatographic column port 67.

A vaporizing column 81 is operably connected in fluid communication between the carrier outlet port 27 of the sample valve 21 and the vaporizing column port 66 of the solvent valve 61. An upstream chromatographic column 83 is operably connected between the chromatographic column port 67 of the solvent valve 61 and an intermediate detecting means 85 with the series combination of the upstream chromatographic column 83 and the intermediate detecting means 85 being connected between the chromatographic column port 67 of the solvent valve 61 and the upstream chromatographic column port 47 of the backflush valve 41. A downstream chromatographic column 87 is connected between the downstream chromatographic column port 46 of the backflush valve 41 and a downstream detecting means 89. Fluid flowing through the detector 89 from the downstream chromatographic column 87 is delivered to a disposal conduit 91.

The automatically controlled valves 34 and 54 illustrated can be any suitable valve means which can be automatically adjusted to provide suitable variations in the resistance to flow therethrough when utilized as illustrated in parallel combination with a fixed flow restriction means or valve. In the preferred embodiment illustrated, the automatic valves 34 and 54 will ordinarily be maintained in either a fully closed or fully open position in order to provide either a free flow of fluid therethrough or a predetermined resistance to flow determined by the parallel flow restriction element. The flow restriction valves 35 and 37 can be any suitable flow restriction means and, although adjustable valve means have been schematically illustrated, nonadjustable restrictions can be utilized. The flow restriction means 53 can be any suitable means for providing an appropriate resistance to flow so that when the bypass valve 54 is in its closed position the loss of carrier gas through the vent conduit 52 and disposal conduit 55 will be kept at a minimum. Although the use of a small diameter or capillary tube is preferred, the flow restriction means 53 can also be a fixed or adjustable valve means similar to the flow restriction valves 35 and 37.

The vaporizer column 81 can be any suitable means for vaporizing the more volatile constituents of a sample introduced thereinto while providing for a minimal spreading of the volatilized material. A preferred vaporizer column 81 is an elongated, unpacked, tubular column having a cross-sectional area which is sufficiently small to prevent appreciable spreading of the vaporized sample constituents and at the same time large enough with respect to the sample size and viscosity to permit rapid vaporization of the more volatile constituents of the sample. The length of the vaporizer column should be sufficient to preclude the possibility of liquid material passing through the vaporizer column into the solvent valve 61 or the upstream chromatographic column 83 but should be short enough to prevent undue spreading of the volatilized constituents during passage therethrough. A preferred vaporizer column 81 is a length of tubing having a cross-sectional area which is about the same or smaller than the cross-sectional area of the chromatographic columns 83 and 87 which are subsequently utilized to separate the volatilized sample constituents. In addition, the vaporizer column 81 preferably has a substantially uniform cross-sectional area. The length of the vaporizer column 81 is preferably no longer than necessary to insure the retention of all sample material which is not vaporized within the vaporizer column 81 consistent with the sample viscosity, flow conditions, and other specific conditions of the particular application involved. The vaporizer column is preferably formed from a relatively nonporous, nonreactive material. A particularly suitable material is stainless steel.

The upstream chromatographic column 83 and the downstream chromatographic column 87 can be any suitable packed chromatographic columns capable of performing the desired separation of the volatilized sample constituents. The columns can be of the same or different lengths and can have the same or different packing material. The intermediate detector 85 and the downstream detecting means 89 can be of any suitable type known in the art such as a flame ionization detector, or a thermal conductivity detector or the like.

In the operation of the preferred embodiment illustrated in FIG. 1, each analysis cycle begins with the sample valve 21, backflush valve 41, and solvent valve 61 in their respective first positions as illustrated. The actuating means of the automatic valves 34 and 35 are operably connected with the actuating means of the backflush valve 41, and when the backflush valve 41 is in its illustrated first position, the automatic valve 34 is open and the automatic valve 54 is closed. A flow of carrier gas is therefore established through the valve 34 and conduit means 36 and is thereafter directed by the backflush valve 41, sample valve 21, and solvent valve 61 in a forward direction to the vaporizer column 81, the upstream chromatographic column 83, the intermediate detector 85, the downstream chromatographic column 87, and the downstream detector 89 to the disposal conduit 91. At the same time a controlled flow of carrier gas is established through the flow restriction valve 37 and conduit 38 and is directed by the backflush valve 41 to the vent conduit 52, flow restriction means 53, and disposal conduit 55. Maintaining the automatic valve 54 in a closed position permits limitation of the flow of carrier gas into the disposal conduit 55 to an amount established by the flow restriction means 53. Although it is within the scope of the invention to omit both the flow restriction means 53 and the automatic valve means 54 and to direct material entering the vent conduit 52 directly into a disposal conduit 55, the illustrated apparatus using the flow restriction means 53 and automatic valve 54 provides for a minimal loss of carrier gas to the disposal conduit 55 when the backflush valve 41 is in its first position as illustrated in FIG. 1.

When the sample valve 21 is in the position illustrated by FIG. 1, liquid sample material is continuously circulated through the sample loop 28 by the pump 14. In a process or other sample material source 11 wherein there is sufficient pressure drop between the conduit 12 removing sample material from the process and the conduit 18 returning material to the process, an adequate flow of sample material through the sample loop 28 may be insured by the pressure differential within the process and use of the pump 14 may be unnecessary. Regardless of the source of sample material flow through the sample loop 28, the pressure and temperature within the sample loop 28 must be maintained at values sufficient to insure the maintenance of sample material in a liquid state and to prevent vaporization of any portion of the sample prior to the switching of the sample valve 21.

In a similar manner, the pump 72 maintains a flow of solvent liquid circulating through the solvent loop 68 associated with the solvent valve 61. Since the solvent liquid is ordinarily a homogeneous liquid material, it is necessary for the pump 72 to circulate only enough material to insure that the solvent loop 68 will be liquid full when the solvent valve 61 is actuated. In order to conserve solvent, the liquid circulated through the solvent loop 68 is returned to the solvent supply 71 for recirculation.

Figure 2:
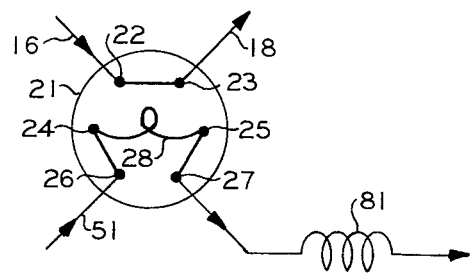
FIG. 2 illustrates the sample valve of FIG. 1 during the time that a sample is being introduced into the system.

To initiate chromatographic analysis of a sample, the sample valve 21 is actuated by any suitable means to inject the sample contained within the sample loop 28 into the gaseous carrier stream flowing to the vaporizer column 81. The sample valve 21 is maintained in its second condition illustrated by FIG. 2 for a time sufficient to permit the entire sample contained within the sample loop 28 to be removed from the sample valve 21 through the carrier outlet port 27 thereof. The sample valve 21 is then immediately returned to the first position illustrated by FIG. 1 in order to permit a continuing flow of sample material therethrough and to establish and maintain a continuing representative sample from the sample source means 11 within the sample loop 28 in preparation for a subsequent sample injection.

As soon as the liquid sample from the sample loop 28 has been injected and the sample valve 21 is returned to its first position, the flow of materials continues to progress as illustrated by FIG. 1. The vaporizer column 81, solvent valve 61, upstream chromatographic column 83, intermediate detector 85, backflush valve 41, downstream chromatographic column 87, and downstream detector 89 are maintained at temperatures and pressures which will insure both the flashing or vaporizing of desired sample constituents within the vaporizer column 81 and the maintenance of the thus-vaporized constituents in a gaseous state for the duration of the analysis process. With the preferred embodiment illustrated, the vaporizer column 81 is maintained at a constant pressure by a regulating valve 32 associated with the carrier gas source 31, and the vaporizer column 81, solvent valve 61, upstream chromatographic column 83, intermediate detector 85, backflush valve 41, downstream chromatographic column 87, and downstream detector 89 are all preferably maintained at a constant preselected temperature.

As the liquid sample enters the vaporizer column 81, the decrease in pressure or increase in temperature, or both, cause the more volatile constituents of the sample to become vaporized with the nonvolatile constituents remaining within the vaporizer column 81. The cross-sectional size of the vaporizer column 81 in relationship to the volume of the liquid sample introduced into it as well as the relative viscosity of the liquid sample and the amount of nonvolatile liquid expected to remain within the vaporizer column 81 are preferably such that the liquid sample will relatively quickly be coated onto the inside wall of the vaporizer column 81 where the nonvolatile portions of the sample will remain until backflushing of the vaporizer column 81 occurs. Coating of the liquid sample on the wall of the vaporizer column in this manner permits rapid vaporization of the more volatile constituents of the sample without undue dissipation or spreading of the vaporized constituents, provides for a continuing unencumbered flow of carrier gas through the vaporizer column 81, and precludes the possibility that a slug or droplet of nonvaporized material will be carried into the solvent valve 61 or upstream chromatographic column 83.

Vaporization of a portion of the liquid sample in the manner described will result in the vaporized sample constituents being carried into the upstream chromatographic column 83 in much the same manner that the same constituents would arrive at the chromatographic column if they had been injected into the carrier stream in a gaseous form by a sample valve. Chromatographic separation of the gaseous sample constituents begins in the upstream chromatographic column 83. The degree of separation accomplished within the upstream chromatographic column 83 can be determined by observing the output of the chromatographic detector 85 located immediately downstream therefrom. While all vaporized constituents of the sample will pass into the chromatographic column 83 and could be eluted therethrough, it may not be necessary to pass all gaseous constituents of the sample into the downstream chromatographic column 87 to obtain the desired analysis. It is, in fact, advantageous to maintain the temperature and pressure conditions within the vaporizer column 81 at a stage which will volatilize slightly more of the sample than it is desired to analyze in order to insure substantially complete vaporization of those constituents which are to be analyzed. For example, when a sample of liquid crude oil is introduced by the sample valve 21 into the vaporizer column 81, and it is desired to determine the amount of $C_5$ and lighter hydrocarbons within the sample, it will ordinarily be necessary to maintain the vaporization column 81 at a temperature which will vaporize some $C_6$ and $C_7$ constituents in order to insure that substantially all $C_5$ constituents are vaporized. Likewise, in order to analyze the $C_{10}$ and lighter hydrocarbons within the same sample, some $C_{11}$ and heavier constituents would necessarily be vaporized at vaporizer column temperatures which would insure substantially complete vaporization of the $C_{10}$ constituents.

Figure 3:
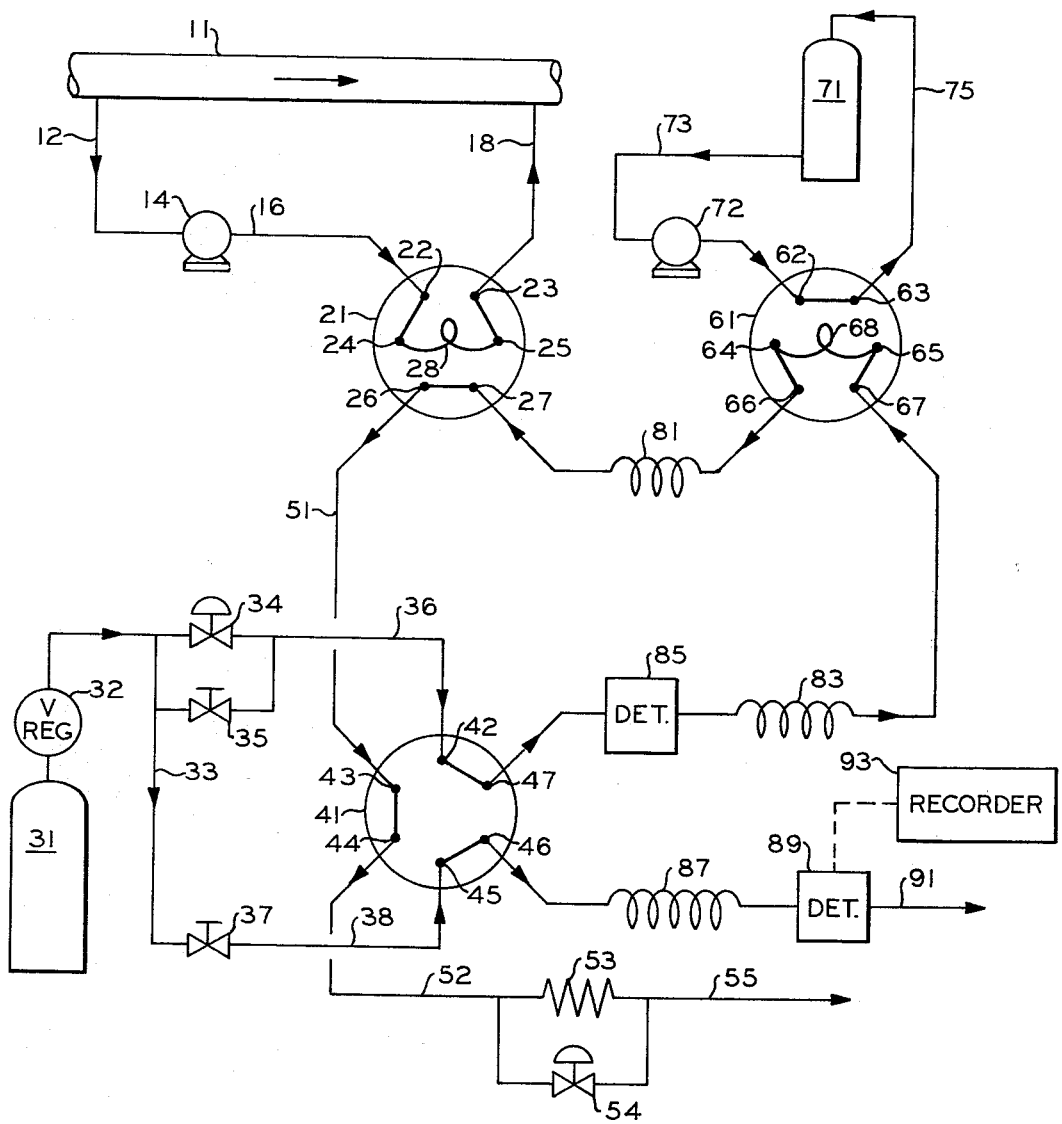
FIG. 3 illustrates the system of FIG. 1 during the time that the system is in the backflush condition.

When the constituents which are desired to be measured have passed the detector 85 and entered the downstream chromatographic column 87, the heavier gaseous constituents remaining within the upstream chromatographic column 83, including any vaporized solvent material, and the liquid constituents remaining within the vaporizer column 81 can be backflushed from the apparatus while elution of the lighter constituents continues through the downstream chromatographic column 87. Backflushing of the upstream chromatographic column 83 and the vaporizer column 81 is accomplished by actuating the backflush valve 41 causing it to assume its second position as illustrated by FIG. 3. Actuation of the backflush valve 41 to initiate backflushing can be accomplished in response to the output of the intermediate detector 85 or, if the time required for the desired constituents to reach and elute through the upstream chromatographic column 83 is known, can be accomplished at a specific time following actuation of the sample valve 21. In the preferred embodiment illustrated the intermediate detector 85 can therefore be used to initially establish the time following introduction of the sample into the vaporizer column 81 at which backflushing will be initiated by operation of the backflush valve 41 and can thereafter be utilized to check to assure that all sample constituents which are to be measured by the downstream detector 89 are in fact reaching the downstream chromatographic column 87 prior to backflushing. In the alternative, the intermediate detector 85 can be omitted once the desired time for backflushing has been established for the same analysis using the same vaporizing column 81 and upstream chromatographic column 83 operating under the same conditions.

Switching of the backflush valve 41 from its first position, illustrated by FIG. 1, to its second position, illustrated by FIG. 3, to initiate backflushing is accompanied by closing of the automatic valve 34 and opening of the automatic valve 54. In addition, the solvent valve 61 is switched from its first position to its second position at the same time as, or immediately following, the switching of the backflush valve 41 to its second position. Delaying the switching of the solvent valve 61 until switching of the backflush valve 41 has been accomplished effectively precludes the possibility of any solvent from the solvent loop 68 being carried into the upstream chromatographic column 83 prior to the time that the flow of carrier gas through the upstream chromatographic column 83 is reversed by the backflush valve 41. Delaying the actuation of the solvent valve 61 in this manner is particularly advantageous where the liquid solvent material being utilized is destructive of either the column packing or a coating on the column packing within the upstream chromatographic column 83.

As illustrated by FIG. 3, switching of the backflush valve 41 and the solvent valve 61 to their second positions along with closing of the automatic valve 34 and opening of the automatic valve 54 results in continuation of chromatographic elution through the downstream chromatographic column 87 while the upstream chromatographic column 83 and vaporizer column 81 are effectively backflushed and made ready for a subsequent sample analysis. The flow restriction valve 37 is preset to provide a flow restriction which will maintain a continuing uniform flow of carrier gas through the downstream chromatographic column 87 following switching of the backflush valve 41 to its second position illustrated by FIG. 3. The resistance to flow provided by the valve 37 will therefore be the same as the combined resistance to flow through the sample valve 21, the vaporizer column 81, the solvent valve 61, the upstream chromatographic column 83, and the intermediate detector 85 when the sample valve 21 and solvent valve 61 are in the positions illustrated by FIG. 1. The downstream chromatographic column 87 is preferably of sufficient length that elution of the lighter sample constituents from the downstream chromatographic column 87 into the downstream detector 89 does not begin until after the backflush valve 41 has been switched to its second position and flow has been established from the second carrier stream conduit 38 into the downstream chromatographic column 87. As the various sample constituents are eluted from the downstream chromatographic column 87, the response of the downstream detector 89 is observed and is preferably recorded by a recording means 93 such as a paper chart recorder or other suitable means, including both digital and analog recording instruments.

While elution of sample constituents through the downstream chromatographic column 87 continues, the carrier fluid flowing into the first carrier stream conduit 36 through the flow restriction valve 35 is directed by the backflush valve 41 in the reverse direction through the intermediate detector 85, the upstream chromatographic column 83, the solvent valve 61, the vaporizer column 81, the sample valve 21, and the conduit 51 connecting the sample valve 21 with the backflush valve 41. In addition, the switching of the solvent valve 61 to its second position effectively injects a predetermined volume of solvent material contained within the solvent loop 68 into the reversed carrier flow. The amount of liquid solvent material so introduced is preferably of sufficient volume to completely wash the remaining liquid portion of the sample material from the vaporizer conduit 81 and is also preferably of sufficient size to prevent the relative volume of the solvent slug from being substantially diminished through the loss of the amount of solvent necessary to wet the walls of the vaporizer column 81. The solvent liquid and that portion of the liquid sample dissolved therein are carried through the backflush valve 41 into the vent conduit 52. With the automatic valve 54 having been placed in its open position at the time backflushing was initiated, the liquid material flows through the valve 54 and into the disposal conduit 55. Since the opening of the valve 54 to provide ready egress of the heavy portion of the sample material and the solvent slug from the apparatus can result in an unnecessarily high rate of reverse flow through the upstream chromatographic column 83 and vaporizer column 81, the flow restriction valve 35 is adjusted so that, upon initiation of backflushing and closure of the automatic valve 34, the flow in the reverse direction through the upstream chromatographic column 83 and vaporizer column 81 is no greater than necessary to provide adequate carrier gas backflushing of the upstream chromatographic column 83, liquid backflushing of the vaporizer column 81, and carrier gas drying of the vaporizer column 81, the portion of the sample valve 21 through which backflushing has taken place, and the conduit 51 connecting the sample valve 21 with the backflush valve 41 prior to the return of the backflush valve 41 to its first position in preparation for analysis of a subsequent sample. When elution of the gaseous sample constituents through the downstream chromatographic column 87 to the downstream detector 89 and backflushing and drying of the upstream chromatographic column 83, vaporizer column 81, and associated equipment is complete, the backflush valve 41 and the solvent valve 61 are returned to their first positions, the automatic valve 34 is opened, and the automatic valve 54 is closed in order to return the system to the condition illustrated by FIG. 1 in readiness to analyze a succeeding sample.

In order to prevent the possible presence of a small amount of liquid solvent remaining within the solvent valve 61, vaporizer column 81, sample valve 21, or conduit 51 from interfering in any way with subsequent sample analysis following backflushing of the vaporizer column 81 with the liquid solvent material, the characteristics of the upstream chromatographic column 83 are preferably such that any remaining vaporized solvent material which is introduced into the upstream column 83 will be unable to elute through the upstream column 83 prior to elution therethrough of the sample constituents desired to be analyzed. The timing of the operation of the backflush valve 41 and the sample valve 21 along with the characteristics of the upstream chromatographic column 83 are preferably such that even vaporized solvent material entering the upstream column 83 prior to the volatilized sample constituents will not elute through the upstream column 83 before the volatile constituents to be analyzed have eluted therethrough and backflushing of the upstream column 83 has been initiated by operation of the backflush valve 41. The exact length and chromatrographic phase utilized within the upstream chromatographic column 83 will be dependent upon the nature of the sample to be analyzed, the particular solvent used, and the exact physical configuration of the sample valve 21, vaporizer column 81, and solvent valve 61 as well as the particular timing of the operation of the backflush valve 41 and the sample valve 21. While the upstream chromatographic column 83 must be as long as necessary to accomplish this effective trapping of solvent material within the context of any particular embodiment of the apparatus and method of the invention, the column 83 is preferably no longer than necessary to accomplish this task with the required margin of safety. The use of the shortest permissible upstream chromatographic column 83 commensurate with the effective use of the column as a solvent trap provides the additional advantage of limiting the size of the upstream chromatographic column 83 which must be replaced in the event that a malfunction within the sample valve 21 and its associated components or the solvent valve 61 and its associated components should result in liquid sample material liquid or solvent being carried into the upstream column 83 thereby contaminating, undesirably altering, or partially destroying the upstream column 83.

Figure 4:
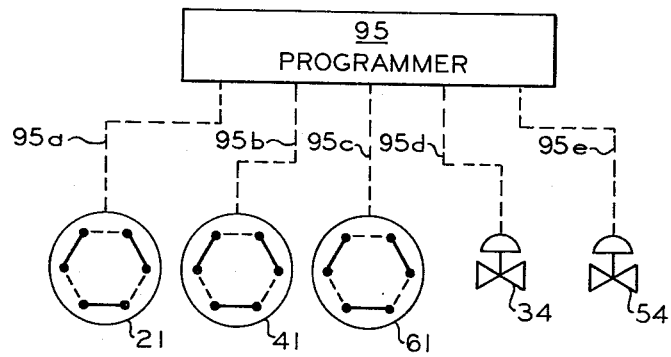
FIG. 4 is a schematic diagram of the control relationship between the apparatus illustrated by FIGS. 1–3 and an automatic programmer which can be utilized in conjunction therewith.
Figure 5:
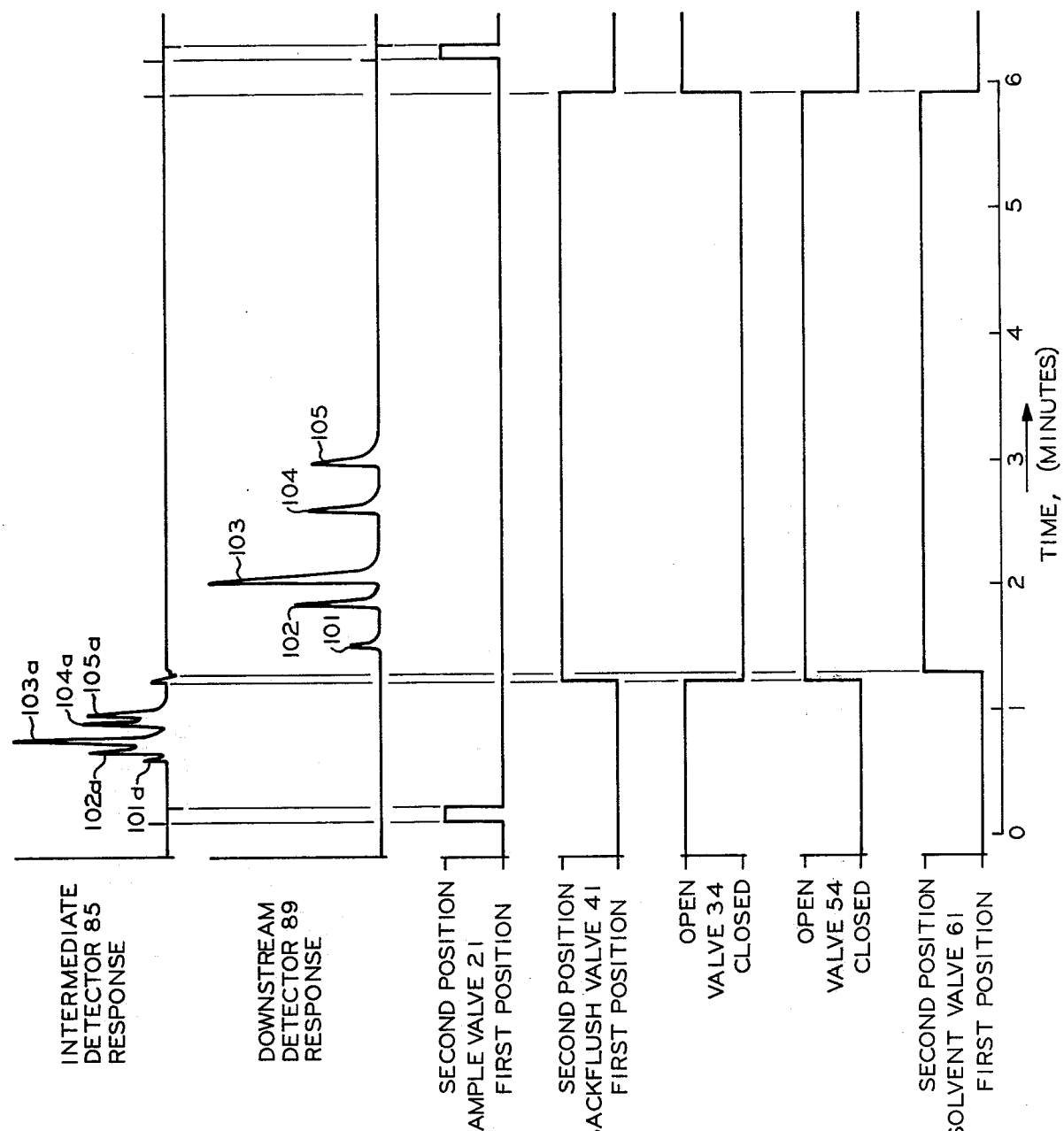
FIG. 5 is an illustration of an exemplary timed relationship of the operation of the method and apparatus of the invention.

A suitable programmer means 95, schematically illustrated by FIG. 4, can be utilized to control the operation of the sample valve 21, backflush valve 41, solvent valve 61, automatic valve 34, and automatic valve 54 in a predetermined timed relationship to insure reliable automatic operation of the apparatus and method of the invention. The control signals $95a - 95e$ provided to the respective valve means can be electrical, mechanical, pneumatic, hydraulic, or combinations of these or other suitable actuating signals which are adapted to operate the particular valve means employed in the practice of the invention. Although the particular timing and sequence of valve operation will vary depending on the nature of the sample and the materials which are to be analyzed as well as the particular solvent liquid employed, FIG. 5 illustrates the timed operation of the preferred embodiment of FIG. 1 in the analysis of the liquid natural gas constituents within the bottoms stream of a crude oil stabilizing column. A further understanding of the operation of the invention is provided by the following example illustrating the operation of a preferred embodiment thereof.

EXAMPLE

Apparatus substantially as illustrated by FIGS. 1–4 was utilized to measure the $C_3-C_5$ components of a sample of crude oil stabilizer bottoms product from which $C_2$ and lighter hydrocarbons had been removed. The apparatus was assembled using three Model IX 6-port valves manufactured by Applied Automation, Inc., Bartlesville, Oklahoma, as the sample valve 21, backflush valve 41, and solvent valve 61. A 1-foot length of 1/16-inch stainless steel tubing was utilized as the vaporizer column 81 and was connected directly to the carrier outlet port 27 of the sample valve 21. The upstream chromatographic column 83 was a 4-foot length of ⅛-inch stainless steel tubing utilizing a chromatographic column packing comprising commercially available DC-200 silicone oil stationary phase on a commercially available 80/100 mesh Chromosorb P diatiomaceous earth solid support. The downstream chromatographic column 89 was a 15-foot column of ⅛-inch diameter and having the same packing material as the upstream chromatographic column 83. The intermediate detector 85 and downstream detector 89 as well as a reference detector, collectively, were the three detectors in a detector assembly number BO-4021, available from Applied Automation, Inc., Bartlesville, Oklahoma.

The sample loop 28 employed with the sample valve 21 was a 2-microliter sample cavity available from the manufacturer of the sample valve as an integral part of the valve 21. The solvent loop 68 utilized was a 1-foot length of ⅛-inch stainless steel tubing connected between the sample loop inlet port 64 and the sample loop outlet port 65 of the solvent valve 61. The sample valve 21, backflush valve 41, solvent valve 61, vaporizer column 81, chromatographic columns 83 and 87, and detectors 85 and 89 were all enclosed in a heated oven maintained at a temperature of 140° F (60° C), a hydrogen carrier gas source 31 was regulated by a regulating valve 32 to provide a supply of 44 psig carrier gas to the conduit means 33. The resistance to flow of the chromatographic system was such that the forward flow of carrier through the vaporizer column 81, upstream chromatographic column 83, and downstream chromatographic column 87 was 40 cc/min; and the restriction flow of the adjustable valve 35 was adjusted to provide a backflush carrier flow rate of 60 cc/min. The adjustable valve 37 was adjusted to provide a continuing forward flow of 40 cc/min. to the downstream chromatographic column 87 when the backflush valve 41 was in the backflush position. A short length of capillary tubing was used as the flow restriction means 53 in order to prevent any unnecessary loss of hydrogen carrier and still maintain a slight forward flow of carrier through the vent conduit 52 when the backflush valve 41 was in the position illustrated by FIG. 1. A Model 102 programmer available from Applied Automation, Inc., Bartlesville, Oklahoma, was utilized to control the timing and sequence of operation of the sample valve 21, normally closed automatic valve 34, backflush valve 41, bypass valve 54, and solvent valve 61. A crude stabilizer bottoms product containing $C_3$ and higher hydrocarbon components and maintained under pressure sufficient to preserve the sample in a liquid state was continuously circulated through the sample loop 28 of the sample valve 21. A hexane liquid solvent was circulated through the solvent loop 68 of the solvent valve 61 to maintain the solvent loop 68 in a liquid full condition.

The responses of the intermediate detector 85 and downstream detector 89 as well as the positions of each of the automatically controlled valves during analysis of the sample for $C_3$–$C_5$ constituents are illustrated by FIG. 5. Within a few seconds following the initiation of a programmed cycle, indicated as time 0 in FIG. 5, the sample valve 21 was switched to its second position, illustrated by FIG. 2, for a period of time sufficient to permit the sample contained within the sample loop 28 to be carried into the vaporizing column 81. The sample valve 21 was thereafter returned to its first position, illustrated by FIGS. 1 and 3, and was maintained in its first position until the initiation of a subsequent sample analysis. The response of the intermediate detector 85 indicates that within slightly more than a minute following the initiation of the programmed cycle the partially separated $C_3$–$C_5$ constituents of the vaporized portion of the sample had passed through the backflush valve 41 into the downstream chromatographic column 87. This condition was confirmed by the presence of an intermediate propane peak 101a, an intermediate isobutane peak 102a, an intermediate normal butane peak 103a, and intermediate isopentane peak 104a, and an intermediate normal pentane peak 105a of the intermediate detector 85. At a time following the passage of the intermediate normal pentane peak 105a through the intermediate detector 85, and prior to the time that any vaporized hexane solvent which may have been remaining in the system upstream of the intermediate chromatographic column 83 from backflushing of the previous sample residue will have had time to elute through the upstream chromatographic column 83, the backflush valve 41 was switched to its second position, illustrated by FIG. 3. At the same time the automatic valve 34 was closed and the automatic valve 54 was opened thereby initiating gas backflushing of the upstream chromatographic column 83 and the vaporizer column 81. Forward flow through downstream chromatographic column 87 continued substantially uninterrupted. Within 2 seconds following the switching of the backflush valve 41, the solvent valve 61 was switched to its second position, illustrated by FIG. 3, in order to inject the slug of hexane solvent into the reversed carrier flow through the vaporizer column 81.

While simultaneous carrier gas backflush of the upstream chromatographic column 83 and liquid backflushing of the vaporizer column 81 was taking place, continuing forward elution through the downstream chromatographic column 87 resulted in the detection by the downstream detector 89 of a propane peak 101, an isobutane peak 102, a normal butane peak 103, an isopentane peak 104, and a normal pentane peak 105. Continuing carrier flow in the forward direction through the downstream chromatographic column 87 and in the reverse direction through the upstream chromatographic column 83 and vaporizer column 81 completed flushing of both chromatographic columns and drying of the hexane liquid from the vaporizer column. At the end of the 6-minute cycle illustrated by FIG. 5 the backflush valve 41, automatic valves 34 and 54, and solvent valve 61 were all returned to their initial positions in preparation for analysis of the subsequent sample.

The exemplary analysis was repeated in 6-minute cycles analyzing a uniform sample for a period of about six weeks. Consistently acccurate analysis of the $C_3$–$C_5$ components of the sample was obtained without interference from liquid sample material or solvent material. The results of the test indicated that the apparatus and method of the invention can be expected to operate accurately for at least a year or more in continuous operation with no substantial loss in effectiveness or accuracy.

Although the invention has been described in conjunction with the preferred embodiment thereof, those skilled in the art will be able to modify the method and apparatus of the invention to analyze various constituents within a wide variety of liquid samples. In addition, the particular vaporizer column, chromatographic column packing, carrier gas, solvent material, and other similar apparatus and materials may be altered within the scope of the invention to accommodate a wide array of various analysis conditions and goals. In addition, those skilled in the art will be capable of integrating the disclosed method and apparatus into new or existing control systems and to interface the method and apparatus of the invention with other process equipment.

Other reasonable variations and modifications can be made by those skilled in the art without departing from the scope of the invention or the appended claims thereto.

What is claimed is:

1. Chromatographic analysis apparatus comprising:
an unpacked tubular vaporizer column means for vaporizing at least a portion of a liquid sample material introduced thereinto, said vaporizer column means having a first end and a second end;
means for providing a flow of a gaseous carrier fluid stream into said first end of said vaporizer column means;
first valve means for introducing a preselected volume of said liquid sample material into said carrier fluid stream flowing into said first end of said vaporizer column means;
first chromatographic column means in fluid communication with said second end of said vaporizer column means for at least partially separating preselected constituents of the vaporized sample material passing therethrough and for delaying the passage of vapors of a solvent liquid therethrough until the passage of all said preselected constituents therethrough has been completed;
second chromatographic column means for receiving said preselected constituents from said first chromatographic column means and for further separating said preselected constituents;
chromatographic detector means for receiving each of said preselected constituents from said second chromatographic column means and delivering a signal responsive to the amount of each said preselected constituent passing therethrough;
third valve means for reversing the flow of fluid through said first chromatographic column means and said vaporizer column means after said preselected constituents have passed from said first chromatographic column means to said second chromatographic column means; and
second valve means for introducing a preselected volume of said solvent liquid into the thus reversed fluid stream flowing into said second end of said vaporizer column means.

2. Apparatus in accordance with claim 1 additionally comprising a programming means for sequentially actuating said first valve means, actuating said third valve means, and actuating said second valve means in a preselected timed sequence.

3. Apparatus in accordance with claim 1 additionally comprising an intermediate detector means interposed between said first chromatographic column means and said second chromatographic column means.

4. Chromatographic analysis apparatus comprising:
an unpacked, tubular vaporizer column means having a first end and a second end;
a first chromatographic column having a first end and a second end;
a second chromatographic column having a first end and a second end;
a downstream chromatographic detector means having an inlet and an outlet, said inlet of said downstream detector being in fluid communication with said second end of said second chromatographic column;
a first carrier gas supply conduit;
a valve connecting conduit;
a second carrier gas supply conduit;
a vent conduit;
backflush valve means for providing fluid communication between said first carrier gas supply conduit and said valve connecting conduit, between said second end of said first chromatographic column and said first end of said second chromatographic column, and between said second carrier gas supply conduit and said vent conduit when said backflush valve means is in a first position, and for providing fluid communication between said first carrier gas supply conduit and said second end of said first chromatographic column, between said valve connecting conduit and said vent conduit, and between said second carrier gas supply conduit and said first end of said second chromatographic column when said backflush valve means is in a second position;
sample valve means for providing fluid communication between said valve connecting conduit and said first end of said vaporizer column means and for injecting a preselected volume of liquid sample material between said valve connecting conduit and said first end of said vaporizer column means; and
solvent valve means for providing fluid communication between said second end of said vaporizer column means and said first end of said first chromatographic column and for injecting a preselected volume of solvent liquid between said second end of said vaporizer column and said first end of said first chromatographic column.

5. Apparatus in accordance with claim 4 wherein said first chromatographic column is adapted to elute preselected vaporized constituents of said sample material therethrough from said first end thereof to said second end thereof prior to elution therethrough of any vaporized portion of said solvent liquid.

6. Apparatus in accordance with claim 5 additionally comprising an intermediate chromatographic detector means having an inlet and an outlet, said inlet of said intermediate detector being in fluid communication with said second end of said first chromatographic column, wherein fluid communication provided with said first chromatographic column by said backflush valve means is established through said outlet of said intermediate chromatographic detector means.

7. Apparatus in accordance with claim 5 additionally comprising automatic programming means for switching said backflush valve means from its first position to its second position immediately following the passage of said preselected vaporized constituents into said first end of said second chromatographic column.

8. Apparatus in accordance with claim 5 wherein the cross-sectional area of said vaporizer column means is substantially uniform and is less than the cross-sectional area of said first chromatographic column or said second chromatographic column.

9. A method for separating preselected constituents within liquid samples having components of differing volatility, said method comprising:
establishing a flow of a gaseous carrier fluid in a forward direction serially through an unpacked, tubular vaporizer column, a first chromatographic column, and a second chromatographic column;
introducing a predetermined volume of a liquid sample into said gaseous carrier fluid entering said vaporizer column;
maintaining said vaporizer column at a preselected pressure and temperature to therein cause vaporization of a portion of said liquid sample, including said preselected constituents;

continuing forward flow of said gaseous carrier fluid to carry said preselected constituents within the vaporized portion of said sample through said first chromatographic column and into said second chromatographic column;

reversing the flow of said gaseous carrier fluid through said first chromatographic column and said vaporizer column at a time following the passage of said preselected constituents through said first chromatographic column but preceding the passage of any vaporized solvent material through said first chromatographic column, while continuing the forward flow of gaseous carrier fluid and said preselected constituents through said second chromatographic column; and injecting a preselected volume of a solvent liquid into the thus reversed flow of carrier fluid at a location between said first chromatographic column and said vaporizer column to remove the remaining liquid portion of said liquid sample from said vaporizer column.

10. A method in accordance with claim 9 addtionally comprising maintaining substantially uninterrupted fluid flow in said forward direction through said second chromatographic column.

11. A method in accordance with claim 10 additionally comprising reestablishing a flow of said gaseous carrier fluid in said forward direction through said vaporizer column and said first chromatographic column, and initiating separation of a subsequent liquid sample.

* * * * *